United States Patent [19]

Abele et al.

[11] Patent Number: 5,303,714
[45] Date of Patent: Apr. 19, 1994

[54] GUIDEWIRE FOR CROSSING OCCLUSIONS IN BLOOD VESSELS

[75] Inventors: John E. Abele, Concord, Mass.; Kevin R. Heath, Providence, R.I.; Mark S. Landman, Sharon; Paul D. McLaughlin, Scituate, both of Mass.

[73] Assignee: Boston Scientific Corporation, Watertown, Mass.

[21] Appl. No.: 62,050

[22] Filed: May 14, 1993

Related U.S. Application Data

[63] Continuation of Ser. No. 611,296, Nov. 9, 1990, abandoned.

[51] Int. Cl.$^5$ .................... A61M 25/00; A61M 29/00
[52] U.S. Cl. .................................. 128/772; 604/170; 606/191
[58] Field of Search .................... 128/656–658, 128/772; 604/164, 170, 280, 282; 606/191

[56] References Cited

U.S. PATENT DOCUMENTS

| | | | |
|---|---|---|---|
| 1,878,671 | 9/1932 | Cantor | 604/170 X |
| 2,022,065 | 7/1932 | Wappler . | |
| 2,047,535 | 10/1932 | Wappler . | |
| 3,196,876 | 7/1965 | Miller | 606/191 X |
| 3,516,412 | 6/1970 | Ackerman . | |
| 3,687,142 | 8/1972 | Leibinzohn . | |
| 3,867,945 | 2/1975 | Long . | |
| 3,928,519 | 12/1975 | Kashiyama et al. . | |
| 3,973,556 | 8/1976 | Fleischhacker et al. . | |
| 3,999,551 | 12/1976 | Spitz et al. | 606/191 X |
| 4,013,079 | 3/1977 | Lindeman . | |
| 4,195,637 | 4/1980 | Grüntzig et al. . | |
| 4,306,566 | 12/1981 | Sinko | 128/658 |
| 4,345,602 | 8/1982 | Yoshimura et al. . | |
| 4,385,635 | 5/1983 | Ruiz | 128/658 |
| 4,388,076 | 6/1983 | Waters | 604/165 |
| 4,388,076 | 6/1983 | Waters . | |
| 4,531,943 | 7/1985 | Van Tassel et al. | 604/280 |
| 4,538,622 | 9/1985 | Samson et al. | 128/772 |
| 4,554,929 | 11/1985 | Samson et al. . | |
| 4,619,274 | 10/1986 | Morrison . | |
| 4,643,194 | 2/1987 | Fogarty | 128/668 |
| 4,665,906 | 5/1987 | Jervis | 128/92 YN |
| 4,690,175 | 9/1987 | Ouchi et al. . | |
| 4,748,986 | 6/1988 | Morrison et al. . | |

(List continued on next page.)

FOREIGN PATENT DOCUMENTS

| | | |
|---|---|---|
| 2017901 | 5/1990 | Canada . |
| 80100445.8 | 8/1980 | European Pat. Off. . |
| 0141006 | 5/1985 | European Pat. Off. . |
| 0363661 | 4/1990 | European Pat. Off. . |
| 0396074 | 11/1990 | European Pat. Off. . |
| 8501444 | 4/1985 | PCT Int'l Appl. ............ 128/772 |
| WO86/05103 | 9/1986 | PCT Int'l Appl. . |
| WO91/19528 | 12/1991 | PCT Int'l Appl. . |

OTHER PUBLICATIONS

Baim et al., "Coronary Angioplasty for Total Occlusion: Ongoing Problems Despite Improving Results," JACC 15; 857–858 (Mar. 15, 1990).

(List continued on next page.)

Primary Examiner—John D. Yasko
Assistant Examiner—Adam J. Cermak
Attorney, Agent, or Firm—Fish & Richardson

[57] ABSTRACT

A guidewire for penetrating an occlusion within a duct or vessel, such as a blood vessel, has an elongated main guidewire body of a small, first diameter. The guidewire is terminated at its distal end with an enlarged resilient tip portion having a lubricious outer surface, and is shaped and constructed to penetrate the occlusion. The guidewire body is constructed to be to be relatively flexible in the distal end corresponding to the enlarged tip and relatively stiffer in portions proximal thereof for manipulation of the wire from its proximal end to cause the distal tip portion to penetrate the occlusion and form a passage therein. In an embodiment, an outer sleeve is slid over the main body and butting against the proximal end of the enlarged tip portion contributes to axial stiffness of the combination to enable manipulation through the occlusion. After placement this sleeve is removed and a dilatation catheter is slid over the main body, and enters the occlusion behind the enlarged tip portion.

33 Claims, 5 Drawing Sheets

U.S. PATENT DOCUMENTS

| | | | |
|---|---|---|---|
| 4,884,579 | 12/1989 | Engelson | 128/772 |
| 4,917,102 | 4/1990 | Miller et al. | 128/772 |
| 4,925,445 | 5/1990 | Sakamoto et al. . | |
| 4,955,862 | 9/1990 | Sepetka . | |
| 4,991,602 | 2/1991 | Amplatz et al. | 128/772 |
| 5,003,990 | 4/1991 | Osypka | 128/772 |
| 5,045,061 | 9/1991 | Seifert et al. | 604/96 |
| 5,059,183 | 10/1991 | Semrad | 604/158 |
| 5,095,915 | 3/1992 | Engelson . | |
| 5,111,829 | 5/1992 | Alvarez de Toledo | 128/772 |
| 5,127,917 | 7/1992 | Niederhauser et al. . | |

OTHER PUBLICATIONS

Ginsburg, "Laser Angioplasty as an Adjunct to Balloon Dilatation," (ch. 36) Endovasvular Surgery (Moore et al., eds.) 389–392 (1989).

Lammer et al., "Recanalization of Arteriosclerotic Occlusions: Excimer Laser", ND-YAG Laser; Guide Wire: A Preliminary Report of a Randomized Trial.

Meier et al., "Magnun Wire for Balloon Recanalization of Chronic Total Coronary Occlusions," Am. J. Cardiol., 64:148–154 (Jul. 15, 1989).

Tonnesen et al., "Femoral Artery Recanalization with Percutaneous Angioplasty and Segmentally Enclosed Plasminogen Activator" (abstract).

Schneider (Europe) AG, Pfizer Hospital Products Group, "Magnum Meier" (Aug. 1990).

Rees, "Treatment of Chronic Coronary Artery Occlusions with an olive tipped guide wire (Magnum) versus Terumo Glidewire," undated.

GUIDEWIRE FOR CROSSING OCCLUSIONS IN BLOOD VESSELS

This is a continuation of application Ser. No. 07/611,296, filed Nov. 9, 1990, now abandoned.

BACKGROUND OF THE INVENTION

The invention relates to medical guidewires for narrow passages of a body, and particularly guidewires that are designed to cross an occlusion of a duct or vessel, such as a coronary artery. A physician introduces the distal end of the guidewire into the body, e.g., via a puncture, and manipulates the flexible tip of the guidewire to enter the desired passageway and follow its convolutions to a treatment site. A dilatation catheter or other medical device may then be advanced over the guidewire to the site.

SUMMARY OF THE INVENTION

According to a first aspect of the invention, a medical guidewire for penetrating an occlusion within a duct or vessel, such as a small blood vessel, has an elongated main guidewire body of a small, first diameter, which is terminated at its distal end with an enlarged resilient tip portion having a lubricious outer surface shaped and constructed to penetrate the occlusion. The guidewire body is constructed to be relatively flexible in the distal end corresponding to the enlarged tip and to be relatively stiffer in portions proximal thereof for manipulation of the wire from its proximal end to cause the distal tip portion to penetrate the occlusion and form a passage therein.

Preferred embodiments of the invention have one or more of the following features. The guidewire is constructed, after formation of the passage in the occlusion, to be advanced to move the tip portion distally beyond the occlusion while advancing a portion of the small main guidewire body across the occlusion, in position to guide a dilatation catheter into the passage. The enlarged tip portion of the guidewire is about the same maximum size as the outer diameter of the deflated balloon of the dilatation catheter. The guidewire is in combination with a dilatation catheter comprised of a catheter shaft carrying a deflated dilatation balloon. The catheter has an internal lumen sized to slide over the main body of the guidewire. The dilatation catheter is constructed thereupon to be advanced over the guidewire across the occlusion to position the balloon thereof in dilatation position in the passage in the occlusion.

Preferred embodiments also include the following. The guidewire body and enlarged tip are cooperatively constructed such that the distal end of the guidewire corresponding to the enlarged tip has greater flexibility at distal portions, than proximal portions. The distal end corresponding to the enlarged tip has gradually increasing flexibility from proximal to distal portions. The enlarged tip portion is tapered to smaller diameters toward the distal end. The tip portion is formed from a plurality of materials, having varying flexibility. The materials are polymers of varying softness. The guidewire body is tapered to smaller diameters toward the distal end. The enlarged tip is of substantially constant cross-sectional diameter and has a curved portion at its most distal end. The lubricious outer surface of the enlarged tip portion is a lubricious hydrophilic plastic.

Preferred embodiments also include the following. The enlarged tip portion is an integral extension of the main body of the guidewire, that serves as the core of the distal portion; the integral extension tapers distally to a narrower dimension at its end, and the hydrophilic plastic is a coating adhered to the exterior of the tapered extension. The guidewire body has a lubricious coating.

Preferred embodiments also include the following. The guidewire is used in combination with an outer sleeve having a lumen sized to slide over the main body of the guidewire and butt against the proximal end of the enlarged tip portion, the sleeve contributing to the axial stiffness of the combination to enable manipulation through the occlusion, and being removable to enable a catheter thereafter to be slid over the guidewire. The outer diameter of the sleeve corresponds generally to the maximum dimension of the distal tip portion of the guidewire. The proximal end of the outer sleeve is maintained in a fixed position relative to the proximal end of the guidewire. The guidewire body comprises a solid core of material. The guidewire is a superelastic or linear elastic alloy. The guidewire is adapted for use in small blood vessels and the main guidewire body has an outer diameter of about 0.018 inches and said distal tip portion has a maximum outer diameter of about 0.035 inches, tapering to a smaller size at its tip. The enlarged distal tip portion comprises a metal core and plastic adhered to the outside thereof. The enlarged tip portion is about 3 cm long. The guidewire body is coated with a lubricious coating.

In another aspect, the invention features a method for positioning a dilatation balloon catheter within an occlusion in a body lumen. The method includes providing a guidewire comprising an elongated main guidewire body of a small, first diameter, the guidewire terminated at its distal end with an enlarged tip portion having a lubricious outer surface shaped and constructed to penetrate the occlusion. The guidewire body is constructed to be relatively flexible in the distal end corresponding to the enlarged tip and relatively stiffer in portions proximal thereof for manipulation of the wire from its proximal end. The guidewire is manipulated in the body lumen in the proximity of the occlusion, maneuvering the enlarged tapered tip portion across the occlusion, the tip portion creating a enlarged passageway in the occlusion. The dilatation balloon catheter is advanced over the guidewire body into the passageway in position for dilatation of the occlusion, the balloon catheter having a predetermined outer diameter of about the same maximum size as the tip portion of the guidewire.

Preferred embodiments include providing the guidewire with an outer sleeve having a lumen sized to slide over the main body of the guidewire and butt against the enlarged tip portion, the sleeve when slid over the main body contributing to the axial stiffness of the combination to enable manipulation through the occlusion and removing the outer sleeve member after the step of manipulating the tip portion across the occlusion and before the step of sliding the dilatation catheter along the guidewire. The body lumen is preferably an occluded coronary artery. The guidewire body and enlarged tip are constructed cooperatively, such that the distal end of the guidewire corresponding to the enlarged member has greater flexibility at distal portions than proximal portions.

DESCRIPTION OF THE PREFERRED EMBODIMENTS

STRUCTURE

Figure 1:
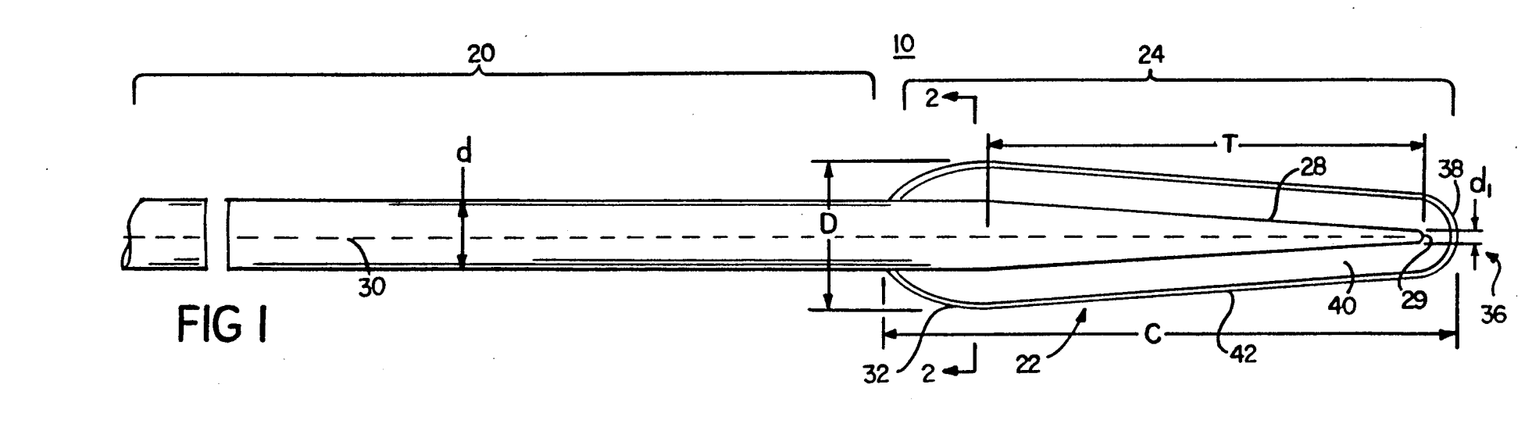
FIG. 1 is a cross section of a guidewire having an enlarged lubricious tip according to the present invention.
Figure 1A:
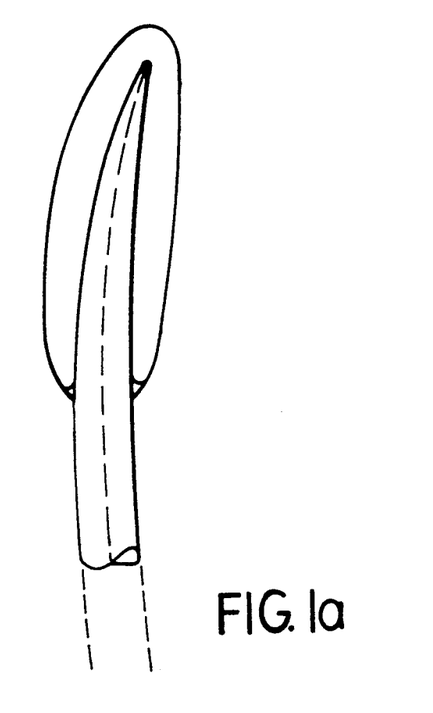
FIG. 1a is a view similar to FIG. 1 showing a curved tip.

Referring to FIG. 1, the guidewire 10 of the invention for particular use in coronary blood vessels has an elongated main wire body 20 and an enlarged distal end portion 24 that has a lubricious outer surface. The elongated wire body 20 is formed of a solid core superelastic alloy, such as Nitinol, or alternatively it is made of a linear elastic material such as titanium, tantalum, stainless steel. In an alternative embodiment, the guidewire is a hollow material, e.g., a superelastic alloy. In the embodiment of FIG. 1, of particular use in small blood vessels, the wire has a diameter, d, of 0.018". A continuation 28 of the wire body at the distal end smoothly tapers along a length T, e.g., 2 cm, from the diameter of the main body, i.e., 0.018", to a distal tip 29 having a diameter $d_1$, e.g., 0.003" to 0.005". This tapered continuation serves as a core of the enlarged distal portion 24. In combination with the outer covering 22 it defines a distal tip region of relatively greater flexibility than the main body, providing a guidewire that smoothly becomes more flexible in the direction of the tip.

Referring to FIG. 1, the enlarged portion 24, extends proximally a limited distance C, e.g., 3 cm, over the tapered core portion 28. As shown in FIG. 1, the covering 22 covers the entire length of the tapered core 28 and partially extends over the main body 26. The enlarged covering 22 is generally axisymmetric with respect to wire axis 30 and has a maximum diameter D of 0.035" at a point 32 located over three-fourths of the distance C from the distal tip. From its maximum diameter, the enlarged covering 22 tapers to a rounded point 38 at its distal end 36 to facilitate penetration into and movement through an occlusion. This taper enables the progressive enlargement of a passage through the occlusion as the guidewire advances. The enlarged covering 22 also smoothly tapers at a greater rate proximally from its maximum diameter to the main body of the guidewire 20 at the proximal end 34, this taper preventing the enlarged portion from snagging upon withdrawal of the guidewire. In particular embodiments, the taper length T may be approximately 10 cm to allow a gradual transition in flexibility from body to tip. The tip of the enlarged portion is preferably curved or angled. In preferred embodiments, the curve is an arc of approximately 60° with a radius of about 0.25". The shape of the tip 29 e.g. the curvature, which causes a deflection of the wire when it encounters objects in the lumen, along with the enlarged nature of the tip, allows the wire to be urged forward with reduced chance that the guidewire will perforate the artery. It will be understood that the taper may begin at a point proximal to or distal from the proximal edge of the enlarged tip and further the taper may be of other desired lengths, e.g., 30 cm.

Figure 2:
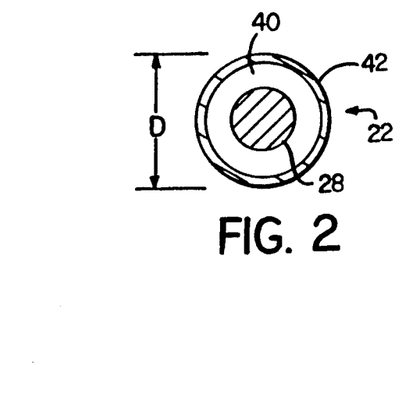
FIG. 2 is an axial cross section of the enlarged lubricious tip taken along line 2—2 of FIG. 1.

Referring to FIGS. 1 and 2, the covering 22 consists of a main layer 40 and a thin hydrophilic, lubricious outer layer 42. The main layer 40 can be made of a low-density, very flexible material such as a polyurethane or EVA (ethylene vinyl acetate), nylon, polyethylene, or PET and can be formed on the distal end of guidewire core 20 by extrusion, dipping or shrink formation. In the embodiment described, the main layer 40 is very flexible relative to the tapered core 28, and adds little mechanical strength to the combination (i.e., the mechanical characteristics of the guidewire core dominate the mechanical characteristics of the enlarged distal portion). The thin, lubricious outer layer 42 is formed of a low coefficient of friction, e.g., hydrophilic, material bonded to the main layer 40. In the figures, the relative thickness of the lubricious outer layer 42, which is typically less than 0.003" (dry thickness), is greatly exaggerated for clarity. Suitable materials are disclosed in "Lubricious Antithrombogenic Catheters, Guidewires and Coatings", U.S. patent application Ser. No. 451,507, filed Dec. 15, 1989, now U.S. Pat. No. 5,135,516, the contents of which are incorporated herein by reference.

As described in the above-referenced application Ser. No. 451,507, the lubricious coating 42 can be a hydrogel, a polymer which is hydrated in the presence of water, and swollen such that a hydrated film contains a greater percentage of water by weight than polymer. This unique property reduces the surface friction of the polymer, creating a "super-slippery" surface that enhances the ability of the device to cross an occlusion. Preferably the coefficient of friction is 0.02–0.6. The thickness of the lubricious outer surface 42 may swell considerably when it is hydrated. Since only the thin coating is swellable, however, and the inner portions of the tip are made of dimensionally stable material, the dimensions of the tip are substantially maintained.

In particular in the above-referenced application Ser. No. 451,507, when dry, the coating is preferably of the order of about 1.0 to 10 μm thick, a 2 to 5 μm coating is typical, although very thin coatings, e.g., of about 0.2–0.3 μm (dry) and much thicker coatings (e.g. more than 10 μm dry) are also possible. As shown in enlarged cross-section view, FIG. 2a, the coating 42 includes a lubricious binding component, shown schematically as 43, and an optional antithrombogenic component, shown schematically as 44. The binding component 43 is a hydrophilic, swellable highly lubricious polymer layer having carboxyl groups (acid groups) with quaternary ammonium cations bonded into the polymer layer. The binding layer 43 acts to bind both the coating to the surface the antithrombogenic component 44 to the coating.

Figure 2A:
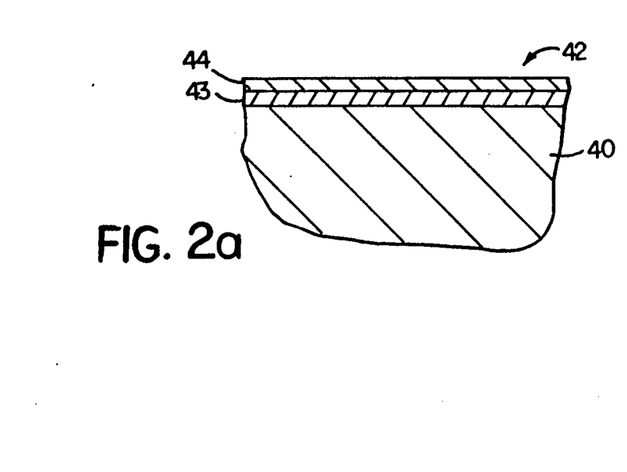
FIG. 2a is an enlarged section view of the lubricious coating of the tip of the guidewire of FIG. 2.

The antithrombogenic component 44 is an antithrombogenic anion, for example, heparin, which is electrostatically attracted to the quaternary ammonium cations of the binding layer in a manner allowing time release of heparin to inhibit clot formation.

In a particular method of forming the coating, the binding component of the thin film is formed on the main layer 40. A lubricious, hydrophilic, water-swellable, acid-containing polymer, for example, polyacrylic acid, is reacted with the binding component. A quaternary ammonium salt, for example a quaternary ammonium halide salt, is then applied to the polymer acid surface to neutralize acid moieties of the polyacrylic acid polymer. The surface is then dried and, if desired, heparin is applied to the surface.

Other suitable polymer coatings are discussed in "Medical Instrument and Method For Making," European Patent Application 0 166 998, by Terumo Corporation, having a reactive functional group covalently bonded with a water-soluble polymer or derivative thereof, such as a cellulosic polymer, maleic anhydride polymer, polyacrylamide, or water-soluble nylon. However, the lubricious coating is not necessarily hydrophilic. A thin coating of other suitable materials having a low coefficient of friction might also be used, e.g., polyurethane, polyethylene, nylon, or a PET or EVA material. In alternative embodiments the wire body is also coated with a lubricious material. The coating also enhances insertion, such as into an outer tube or into a catheter shaft. It will also be understood that drugs such as antiproliferatives may be incorporated into suitable polymer coatings.

Figure 3:
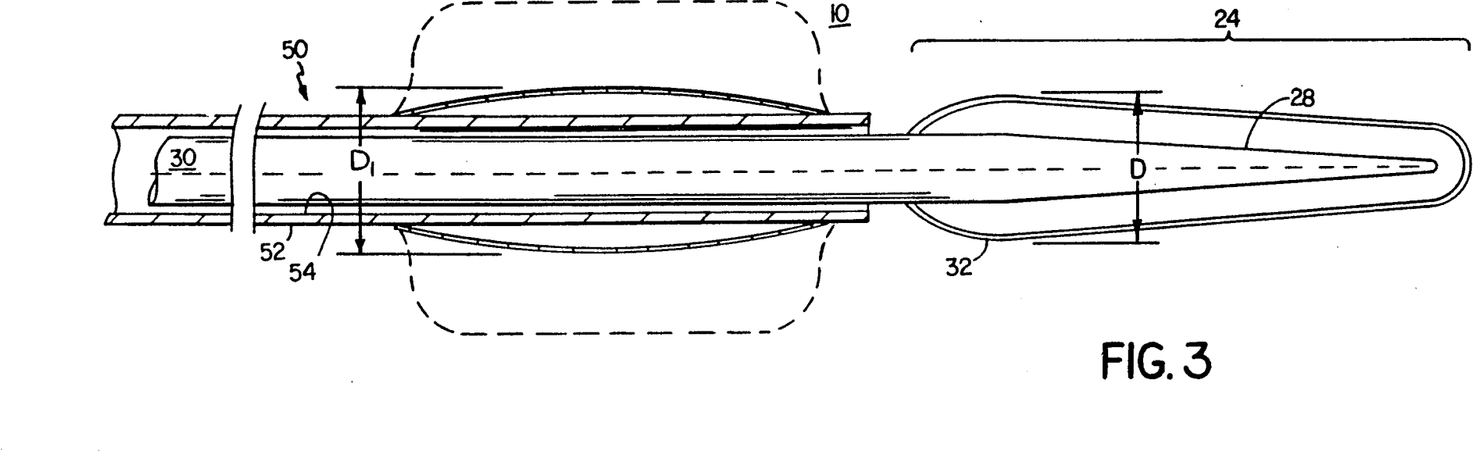
FIG. 3 is a cross section of a dilatation balloon catheter slid over the guidewire of FIG. 1.

The guidewire 10 may be used in combination with an angioplasty balloon catheter 50 as shown in FIG. 3. The balloon catheter 50 consists of a catheter body 52 having an internal lumen 54 sized to allow the catheter body to slide along the length of guidewire main body 26. An angioplasty balloon 56, shown here in its deflated condition, is disposed near the distal end of the catheter 50. The outer diameter $D_1$ of the deflated balloon 56 generally corresponds to the maximum diameter D of the enlarged distal end portion 24 of the guidewire. When in dilatation position, the balloon 56 is inflated by passing a fluid through the lumen 54 of the catheter body. Once inflated, as shown as the dotted line, the balloon becomes larger, as determined by preselection of the balloon size.

The invention is suited for the treatment of various occluded ducts and vessels, such as blood vessels. The dimensions of the guidewire and other portions of the invention are varied according to the dimensions of the duct or vessel to be treated. For example, a large femoral artery or a large duct requires a relatively large guidewire and tip.

Figure 4:
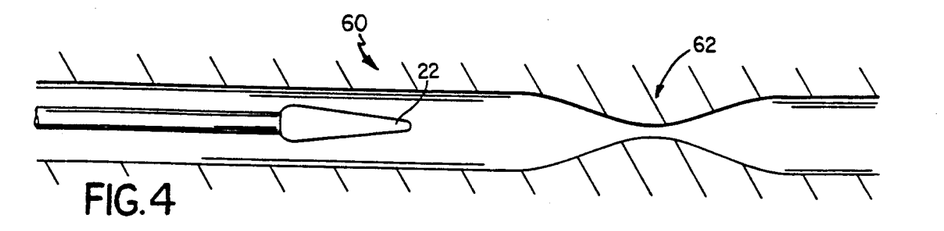
FIGS. 4–4b are schematic views of a guidewire having an enlarged lubricious tip of the present invention positioned in a body lumen.
Figure 4A:
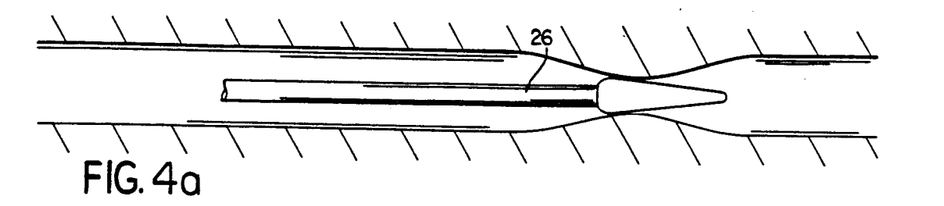
Figure 4B:
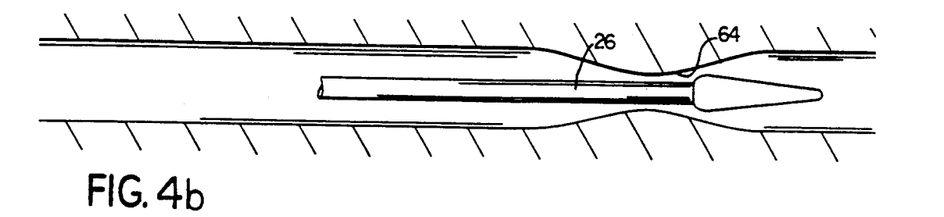
Figure 4C:
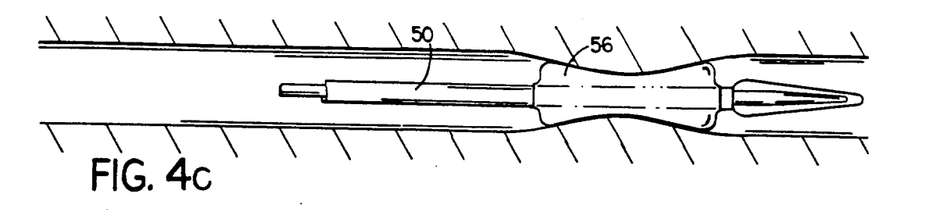
FIGS. 4c–4d show a dilatation catheter positioned over the guidewire.
Figure 4D:
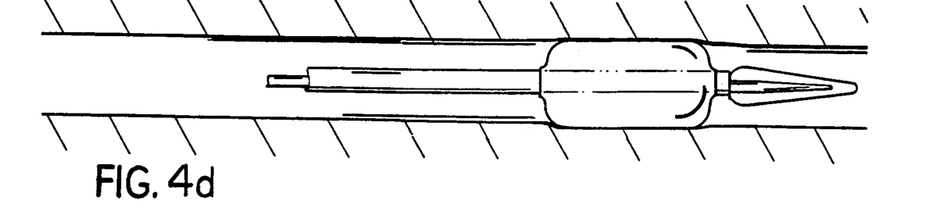

The guidewire 10 is especially suited for the treatment of vascular ailments, such as dilatation of a vascular occlusion in a small blood vessel, in particular a coronary artery. Referring to FIG. 4, the distal end of the guidewire is inserted and positioned in coronary artery 60, using standard guidewire positioning procedures as known in the art. As shown in FIG. 4 the guidewire confronts an occlusion 62 of the coronary artery. Application of axial pressure on the proximal end of the guidewire advances the distal end of the guidewire and the enlarged lubricious end portion 24 to the occlusion site. Further axial pressure causes the lubricious end portion 24 to penetrate the occlusion 62 (FIG. 4a) by gradually and gently widening the occlusion and eventually cross occlusion 62 (FIG. 4b). Typically, the user rotates the wire as it is urged forward. Once the guidewire has crossed the occlusion 62, only the smaller diameter main body of the guidewire resides in the newly formed perforation or passage in the occlusion. The angioplasty balloon catheter 50 is then slid over the guidewire from the proximal end, and guided into the passage through the occlusion. Because the diameter of the deflated balloon 56 is approximately the same as that of the enlarged distal portion of the guidewire, the distal end of the ballon catheter fits in the perforation 64 made by the guidewire (FIG. 4c). once positioned in the occlusion, the angioplasty balloon 56 can be inflated in normal fashion (FIG. 4d) until the occlusion is fully opened, at which time the catheter and guidewire can be withdrawn as a unit. If, however, the passage is not completely opened by the fully inflated balloon, the dilatation balloon catheter can be removed and a larger dilatation balloon inserted using the in-place guidewire. It will be appreciated that the enlarged portion of the guidewire, once inserted in the blood vessel and pushed past the occlusion, will not need to be removed before the dilatation is completed.

The wire core and enlarged member are cooperatively constructed to facilitate passage of the guidewire through a portion of a body lumen narrowed by disease, e.g., a blood vessel narrowed by plaque. The guidewire is of sufficient strength and flexibility to avoid kinking and enable good torque control as the wire is passed through tortuous lumens and urged against an occluded area by axial force from the proximal end, while the enlarged tip, which minimizes the likelihood that the guidewire could perforate the lumen wall, is of the proper resiliency and slipperiness to facilitate passage, e.g., by a gradual enlargement of the occluded area. The performance of the guidewire is selected by coordination of the flexibility and strength contributed by the guidewire and tip and the slipperiness of the tip. The guidewire is constructed to be relatively flexible in the distal end corresponding to the enlarged tip and relatively stiffer in portions proximal thereof. The guidewire and the tip may be tapered or of constant diameter. Preferably the end corresponding to the tip has gradually increasing flexibility from proximal portions to distal portions.

Figure 5:
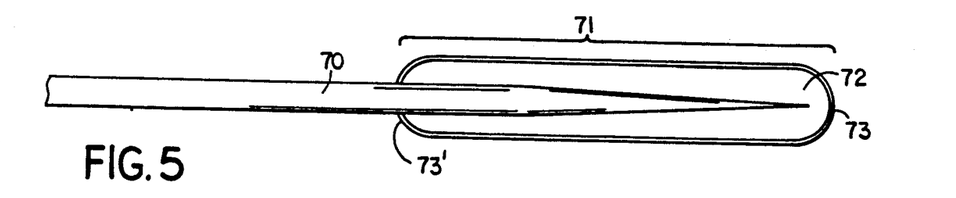
FIG. 5 is a cross section of an alternative embodiment of the guidewire having an enlarged lubricious tip of constant outer diameter and a tapered core.

Referring to FIG. 5, another embodiment of the invention is shown where the enlarged tip 71 has a generally cylindrical cross sectional configuration, with a constant outer diameter and rounded ends 73, 73'. The guidewire 70 is tapered at its distal end. As a result, the amount of material 72 increases distally in proportion to the decrease in the diameter of the inner core 70. Thus, the flexibility of the enlarged tip 71 increases in the distal direction.

Figure 6:
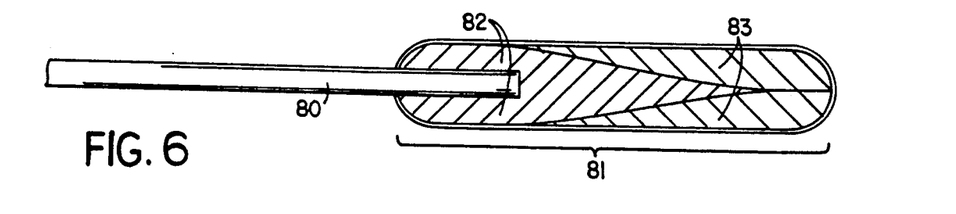
FIG. 6 is a cross section of an alternative embodiment of the guidewire having an enlarged lubricious tip of constant outer diameter and a core of constant diameter, the tip being increasingly flexible from its proximal end to its distal end due to the configuration of the material comprising the tip.

Referring to FIG. 6, another embodiment of the invention is shown where the guidewire 80 has a constant diameter and the enlarged lubricious tip 81 also has a constant outer diameter. The increasing flexibility from the proximal end to the distal end is due to the configuration of the material in the tip 81. In the embodiment shown, the enlarged tip 81 is comprised of two materials. A tear-shaped configuration 82 of high density polyethylene or of a PET substance tapers distally to a point, while the tapering portion of the tear-shaped configuration 82 is covered with distally increasing amounts of a soft or low-density polyethylene or of an EVA material 83.

Figure 7:
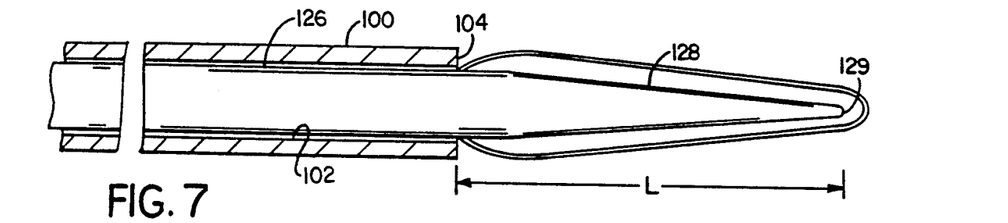
FIG. 7 is a cross section of a guidewire having an enlarged lubricious tip of the present invention having an outer sleeve for added axial stiffness.

Referring to FIG. 7, another embodiment of the invention is shown where a hollow outer sleeve 100 is combined with the guidewire to confer added stiffness to the guidewire. Prior to entry into the body, to enhance the guidewire's pushability and torquability, a thin stiff sleeve 100, (such as a cross wound multifilar tube, e.g. a Cragg wire TM, (available from Boston Scientific Corp., Watertown, Mass.)) is slid over the core 126 of the guidewire. The distal end 104 of the sleeve 100 is positioned a distance L, e.g., 8 cm, from the distal end 129 of the tapered core 128 to provide differential stiffness to the guidewire in its distal region. The sleeve and guidewire are positioned as a unit in the occluded blood vessel, and after the guidewire and sleeve have crossed the occlusion and are in a position analogous to FIG. 4b, the connection at the proximal ends is undone and the hollow outer sleeve is removed, leaving the guidewire in position to accept an angioplasty balloon catheter as described above. In alternative embodiments, the outer sleeve is made from a stiff plastic, such as polyimide, or a superelastic alloy.

Figure 8:
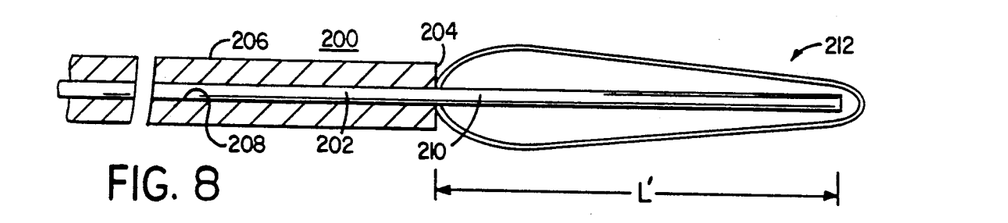
FIG. 8 is a cross section of an alternative embodiment of the guidewire having an enlarged lubricious tip of the present invention.

Referring now to FIG. 8, another embodiment of the invention is shown where the main body of the guidewire 200 comprises an internal wire 202 within an outer sleeve member 206. An extension of the wire core 202 extends distally a length L' (e.g., 3-10 cm) from the distal end 204 of the outer sleeve member 206. The core 202 is formed of a superelastic alloy, such as Nitinol, and the extension of the core into an enlarged end portion 212 has a uniform diameter (e.g., no substantial taper) of 0.005" over its length. The outer sleeve member 206 is formed from a thin-walled hypodermic tube having an outer diameter of 0.018". The internal lumen 208 of the sleeve member has an internal diameter equal to the outer diameter of internal core 202 and is fixedly attached to the outer surface of the internal core 202. The enlarged covering 212 is tapered with a lubricious surface provided on the distal end portion 210 of the internal core in the manner described above. The lubricious covering, as described above, is very flexible so that the mechanical properties of the internal core 202 dominate the properties of the distal tip portion 210 of the guidewire.

Figure 9:
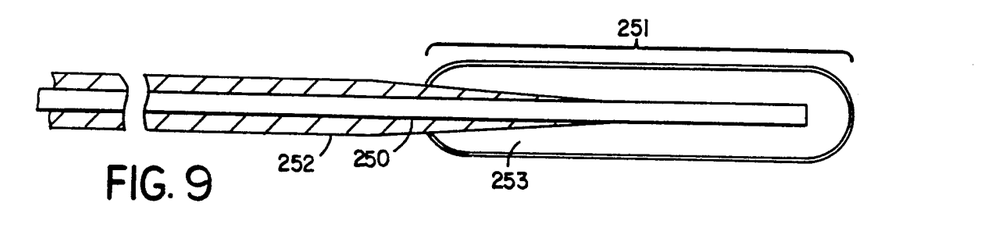
FIG. 9 is a cross section of an alternative embodiment of the guidewire having an inner core of constant diameter, an enlarged lubricious tip of constant outer diameter, and an outer sleeve tapered at its distal end.

Referring to FIG. 9, another embodiment of the invention is shown where the guidewire 250 has a constant diameter and the enlarged lubricious tip 251 has a constant outer diameter. In this embodiment, however, the fixed outer sleeve 252 tapers toward its distal end, which extends partly into the enlarged tip 251. The amount of lubricious material 253, therefore, distally increases to provide distally increasing flexibility. In preferred embodiments, the taper length is approximately 10 cm to achieve a gradual transition from the stiff body to the flexible tip.

Figure 10:
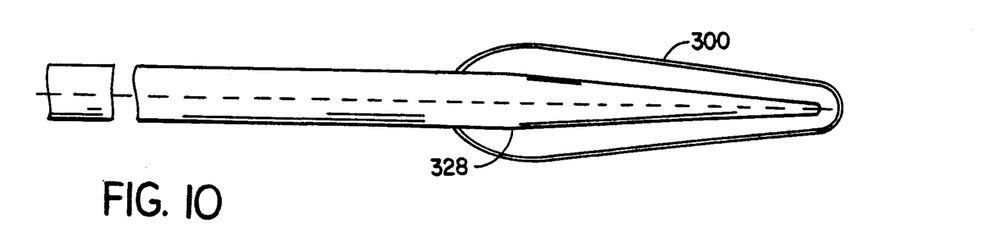
FIG. 10 is a cross section of an alternative embodiment of the guidewire having a tapered, enlarged lubricious tip of the present invention.

Referring to FIG. 10, another embodiment of the invention is shown where the guidewire has an enlarged lubricious tapered covering 300 as provided on the distal end portion 328 of the internal core in the manner described above. The lubricious tapered covering 300 is formed from a suitable elastomeric material alone, (e.g., polyurethane) and does not include an additional layer as discussed above in conjunction with the embodiment in FIG. 1.

Other embodiments are possible. For example, the guidewire may be constructed and dimensioned for use in various vessels such as the ureter, urethra and bile ducts.

Numerous other embodiments are within the spirit and scope of the invention and the following claims:

We claim:

1. A medical guidewire comprising:
   an elongated main guidewire body having selected stiffness characteristics along its length to allow the guidewire to be urged through a narrow, torturous body lumen by application of forces at a proximal end, and
   a composite enlarged distal end portion comprised of an extension of said main guidewire body and a surrounding enlarged soft outer polymeric element having a diameter larger than the diameter of portions of said main guidewire body proximal of said enlarged distal end portion, the portion of said guidewire body in the distal part of said enlarged distal end portion being of smaller diameter than the portion of said guidewire body in the proximal part of said enlarged distal end portion, the flexibility of said enlarged distal end portion being determined over substantially all of its length predominantly by the respective portions of the guidewire body therewithin.

2. The guidewire of claim 1 wherein said soft polymeric element extends distally beyond the distal portion of said main guidewire body to form a soft, more distal tip for gently penetrating said occlusion as said guidewire is urged axially distally.

3. The guidewire of claim 2 wherein said enlarged distal end portion has a curve at its most distal end.

4. The guidewire of claim 1 wherein, in at least portions of the enlarged distal end portion, the thickness of said soft polymeric element is about equal to or greater than the radius of the corresponding portion of the wire body.

5. The medical guidewire of claim 1 wherein said enlarged distal end portion is about 3 cm long.

6. The guidewire of claim 1 or 5 wherein the distal extremity of said extension of said main guidewire body is about 0.003 to about 0.005 inch diameter.

7. The guidewire of claim 6 wherein said guidewire has a diameter for use in small blood vessels and said enlarged distal end portion has an outer diameter no greater than about 0.035 inch.

8. The guidewire of claim 7 wherein said main guidewire body proximal of said extension has an outer diameter of about 0.018 inch.

9. The guidewire of claim 1 wherein said guidewire body and enlarged distal end portion are cooperatively constructed such that said enlarged distal end portion has greater flexibility distally, than proximally.

10. The guidewire of claim 9 wherein said enlarged distal end portion has gradually increasing flexibility from proximal to distal ends.

11. The guidewire of claim 10 wherein said guidewire body is tapered to smaller diameters toward the distal end.

12. The guidewire of claim 10 or 11 wherein said enlarged distal end portion is tapered to smaller diameters toward the distal end.

13. The guidewire of claim 1 wherein said guidewire body is comprised of a superelastic metal alloy.

14. The guidewire of claim 1 wherein said guidewire body is comprised of a linear elastic metal.

15. The guidewire of claim 13 or 14 wherein said main guidewire body comprises a solid wire.

16. The guidewire of claim 1 wherein said polymeric element is formed by extrusion.

17. The guidewire of claim 16 wherein said outer polymeric element is formed of a nylon polymer.

18. The guidewire of claim 1 wherein said polymeric element is formed by dipping or shrink formation over an extension of said main guidewire body.

19. The guidewire of claim 1 wherein said guidewire body has an exterior surface that includes a lubricious coating.

20. The guidewire of claim 1 wherein the exterior surface of said soft outer polymer element includes a thin hydrophilic coating of a hydrogel polymer.

21. The guidewire of claim 1 wherein a lubricious surface on the exterior of said enlarged distal end portion is defined by a material from the group consisting of polyurethane, hydrogel, polyacrylic acid, cellulosic polymer, maleic anhydride polymer, polyacrylamide, polyethylene, EVA, PET and nylon.

22. The guidewire of claim 1 being of sufficient length and stiffness such that after formation of said passage in said occlusion, said guidewire can be advanced to move said enlarged distal end portion distally beyond said occlusion while advancing a portion of said main guidewire body across said occlusion, in position to guide a dilitation catheter into said passage in said occlusion.

23. The guidewire of claim 22 adapted for use with a predetermined dilatation catheter comprised of a catheter shaft carrying a deflated dilatation balloon,
said catheter having an internal guidewire lumen of predetermined size, the main guidewire body of said guidewire having a diameter less than said predetermined size of said guidewire lumen and of length constructed to enable said dilatation catheter to be advanced over said guidewire across said occlusion to position the balloon thereof in dilatation position in the passage of said occlusion.

24. The guidewire of claim 23 wherein said dilitation catheter is of predetermined outer diameter, the maximum diameter of said enlarged distal end portion of said guidewire having about the same diameter as the outer diameter of the deflated balloon of said catheter, to form a passage in said occlusion that can readily receive said balloon.

25. The medical guidewire of claim 1 in combination with an outer sleeve having a lumen sized to slide over said main guidewire body and butt against the proximal end of said enlarged distal end portion, said sleeve when slid over said main guidewire body contributing to the axial stiffness of said combination to facilitate manipulation through said occlusion, said sleeve being removable to enable a catheter thereafter to be slid over said guidewire.

26. The guidewire of claim 25 wherein the outer diameter of said sleeve corresponds generally to the maximum diameter of said enlarged distal end portion of said guidewire.

27. The guidewire of claim 1 in combination with a sleeve that is fixedly attached to said guidewire for contributing to the axial stiffness of the combination to facilitate manipulation through said occlusion.

28. The guidewire of claim 27 wherein said enlarged distal end portion is about 3 cm long and, in at least portions of the enlarged distal end portion, the thickness of said soft polymeric element is about equal to or greater than the radius of the corresponding portion of the wire body.

29. A medical guidewire comprising:
an elongated solid main guidewire body having selected sitffness characteristics along its length to allow the guidewire to be urged through a narrow, torturous body lumen by application of forces at a proximal end, and
a composite enlarged distal end portion comprised of an extension of said main guidewire body and a surrounding enlarged, extruded soft outer polymeric element having a diameter larger than the diameter of portions of said main guidewire body proximal of said enlarged distal end portion, the portion of said guidewire body in the distal part of said enlarged distal end portion being of smaller diameter than the portion of said guidewire body in the proximal part of said enlarged distal end portion, the flexibility of said enlarged distal end portion being determined over substantially all of its length predominantly by the respective portions of the guidewire body therewithin,
the distal extremity of said extension of said main guidewire body being about 0.003 to about 0.005 inch diameter, and said soft polymeric element extending distally beyond the distal extremity of said main guidewire body to form a soft, most distal tip for gently penetrating said occlusion as said guidewire is urged axially distally.

30. A method for positioning a dilatation balloon catheter within an occlusion in a body lumen comprising:
providing a guidewire comprising an elongated main guidewire body having selected stiffness characteristics along its length to allow the guidewire to be urged through a narrow, torturous body lumen by application of forces at a proximal end, and
a composite enlarged distal end portion comprised of an extension of said main guidewire body and a surrounding enlarged soft outer polymeric element having a diameter larger than the diameter of portions of said main guidewire body proximal of said enlarged distal end portion, the portion of said guidewire body in the distal part of said enlarged distal end portion being of smaller diameter than the portion of said guidewire body in the proximal part of said enlarged distal end portion, the flexibility of said enlarged distal end portion being determined over substantially all of its length predominantly by the respective portions of the guidewire body therewithin,
manipulating said guidewire in said body lumen in the proximity of said occlusion,
maneuvering said enlarged distal end portion across said occlusion, said enlarged distal end portion creating an enlarged passageway in said occlusion; and
advancing a dilitation balloon catheter over said guidewire body into said passageway in position for dilitation of said occlusion, said balloon catheter having a predetermined outer deflated diameter of about the same maximum diameter as the enlarged distal end portion of said guidewire.

31. The method of claim 30 further comprising:
providing said guidewire with an outer sleeve having a lumen sized to slide over the main body of said guidewire and butt against said enlarged distal end portion, said sleeve when slid over the main body constructing to the axial stiffness of said combination to facilitate manipulation through said occlusion; and removing said outer sleeve member after the step of manipulating said tip portion across said occlusion and before the step of sliding said dilitation balloon catheter along said guidewire.

32. The method of claim 30 wherein said body lumen is an occluded coronary artery.

33. The method of claim 30 further comprising constructing said guidewire body and enlarged distal end portion cooperatively, such that said enlarged polymeric distal end portion has greater flexibility distally, than proximally.

* * * * *

UNITED STATES PATENT AND TRADEMARK OFFICE
CERTIFICATE OF CORRECTION

PATENT NO. : 5,303,714
DATED : April 19, 1994
INVENTOR(S) : John E. Abele, et. al.

It is certified that error appears in the above-indentified patent and that said Letters Patent is hereby corrected as shown below:

Col. 9,
In claim 22 at line 35, change "dilitation" to --dilatation--;
Col. 9,
In claim 24 at line 49, change "dilitation" to --dilatation--;
Col. 10,
In claim 29 at line 13, change "sitffness" to --stiffness--;
Col. 10,
In claim 30 at lines 66 and 68, change each instance of "dilitation" to --dilatation--.

Signed and Sealed this

Twenty-first Day of November, 1995

Attest:

BRUCE LEHMAN

Attesting Officer

Commissioner of Patents and Trademarks